US008263376B2

(12) United States Patent
Sugio et al.

(10) Patent No.: US 8,263,376 B2
(45) Date of Patent: *Sep. 11, 2012

(54) LIPOXYGENASE

(75) Inventors: Akiko Sugio, Manhattan, KS (US); Shinobu Takagi, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/076,803

(22) Filed: Mar. 31, 2011

(65) Prior Publication Data

US 2011/0183865 A1    Jul. 28, 2011

Related U.S. Application Data

(60) Continuation of application No. 11/832,472, filed on Aug. 1, 2007, now abandoned, which is a division of application No. 10/473,533, filed as application No. PCT/DK02/00251 on Apr. 18, 2002, now Pat. No. 7,264,954.

(60) Provisional application No. 60/286,031, filed on Apr. 24, 2001.

(30) Foreign Application Priority Data

Apr. 20, 2001 (DK) .......................... PA 2001 00631

(51) Int. Cl.
*C12N 9/02* (2006.01)
*C12P 2/06* (2006.01)
*C11D 3/386* (2006.01)

(52) U.S. Cl. ............................ 435/189; 426/20; 510/320
(58) Field of Classification Search ........................ None
See application file for complete search history.

(56) References Cited

U.S. PATENT DOCUMENTS

| 6,204,037 B1 | 3/2001 | Brash et al. |
| 2004/0029225 A1 | 2/2004 | Akiko et al. |

FOREIGN PATENT DOCUMENTS

| JP | 2000/106832 | 6/1998 |
| WO | WO 00/60093 A1 | 10/2000 |
| WO | WO 01/29227 | 4/2001 |
| WO | WO 01/79560 A3 | 10/2001 |
| WO | WO 01/90323 A3 | 11/2001 |
| WO | WO 02/20730 A2 | 3/2002 |

OTHER PUBLICATIONS

Chica et al, Curr Opin Biotechnol, vol. 16, No. 4, pp. 378-384 (2005).
Guo et al, PNAS, vol. 101, No. 25, pp. 9205-9210 (2004).
Hornsten et al, Eur J Biochem, vol. 269, pp. 2690-2697 (2002).
Su et al, Eur J Biochem, vol. 273, No. 21, pp. 13072-13079 (1998).
JP 2000-106832—Abstract.

*Primary Examiner* — Tekchand Saidha
*Assistant Examiner* — Md. Younus Meah
(74) *Attorney, Agent, or Firm* — Kristin J. McNamara

(57) ABSTRACT

The present disclosure relates to an isolated lipoxygenase. The lipoxygenase of the present disclosure includes polypeptide with at least 80% sequence homology to the mature peptide shown in SEQ ID NO: 2. Lipoxygenase of the present disclosure is suitable for use in, among other things, baking and in detergent compositions.

13 Claims, No Drawings

SEQUENCE LISTING

```
<160> NUMBER OF SEQ ID NOS: 4

<210> SEQ ID NO 1
<211> LENGTH: 1973
<212> TYPE: DNA
<213> ORGANISM: Magnaporthe salvinii
<220> FEATURE:
<221> NAME/KEY: CDS
<222> LOCATION: (1)..(381)
```

```
<220> FEATURE:
<221> NAME/KEY: mat_peptide
<222> LOCATION: (52)..()
<220> FEATURE:
<221> NAME/KEY: CDS
<222> LOCATION: (501)..(1970)

<400> SEQUENCE: 1
```

| | | | | | | | | | | | | | | | | |
|---|---|---|---|---|---|---|---|---|---|---|---|---|---|---|---|---|
| atg | cgc | atc | gga | ctc | ttg | gcc | ttc | gcc | gtc | gcg | gcg | cgc | tat | gtg | gaa | 48 |
| Met | Arg | Ile | Gly | Leu | Leu | Ala | Phe | Ala | Val | Ala | Ala | Arg | Tyr | Val | Glu | |
| | -15 | | | | -10 | | | | | -5 | | | | | | |
| gcg | ctg | cca | gtc | gcg | agc | ggc | gaa | gaa | gtg | gcc | tcg | tcg | tcc | gct | ccg | 96 |
| Ala | Leu | Pro | Val | Ala | Ser | Gly | Glu | Glu | Val | Ala | Ser | Ser | Ser | Ala | Pro | |
| -1 | 1 | | | | 5 | | | | | 10 | | | | | 15 | |
| acg | acg | ctg | ccc | tcg | acg | tcg | agc | agc | tct | gcg | ctt | ccc | tcc | ccg | acc | 144 |
| Thr | Thr | Leu | Pro | Ser | Thr | Ser | Ser | Ser | Ser | Ala | Leu | Pro | Ser | Pro | Thr | |
| | | | | 20 | | | | | 25 | | | | | 30 | | |
| aag | tac | acg | ctt | ccc | cac | gag | gac | ccc | aac | ccg | gaa | gcg | agg | aag | gcc | 192 |
| Lys | Tyr | Thr | Leu | Pro | His | Glu | Asp | Pro | Asn | Pro | Glu | Ala | Arg | Lys | Ala | |
| | | | 35 | | | | | 40 | | | | | 45 | | | |
| gag | ata | gcg | tta | aag | agg | gga | ggg | ttc | ctc | tac | gga | ccc | tcc | acc | ctg | 240 |
| Glu | Ile | Ala | Leu | Lys | Arg | Gly | Gly | Phe | Leu | Tyr | Gly | Pro | Ser | Thr | Leu | |
| | | | 50 | | | | | 55 | | | | | 60 | | | |
| ggc | cag | act | acc | ttt | tac | ccc | agc | ggg | acc | ctg | ggg | acc | gcc | atg | tcg | 288 |
| Gly | Gln | Thr | Thr | Phe | Tyr | Pro | Ser | Gly | Thr | Leu | Gly | Thr | Ala | Met | Ser | |
| | 65 | | | | | 70 | | | | | 75 | | | | | |
| caa | cgc | gac | cag | gcc | ctc | tgg | ctc | agg | gat | gca | gag | aac | caa | acg | ata | 336 |
| Gln | Arg | Asp | Gln | Ala | Leu | Trp | Leu | Arg | Asp | Ala | Glu | Asn | Gln | Thr | Ile | |
| 80 | | | | | 85 | | | | | 90 | | | | | 95 | |
| aca | gcg | tat | cgt | gaa | gcc | aac | gag | aca | ctg | agg | gat | atc | cag | agc | | 381 |
| Thr | Ala | Tyr | Arg | Glu | Ala | Asn | Glu | Thr | Leu | Arg | Asp | Ile | Gln | Ser | | |
| | | | | 100 | | | | | 105 | | | | | 110 | | |

```
gtatgtgtcg agccgtgttt atgcgttcca atcattctct gtgctcctgt ccgtccccgc      441
ccggggttac agccaagccg attcagtagc taactcggaa tgtctggttt gctctgcag       500
```

| | | | | | | | | | | | | | | | | |
|---|---|---|---|---|---|---|---|---|---|---|---|---|---|---|---|---|
| cat | ggc | ggt | ctc | aag | acg | ctt | gac | gac | ttc | gcg | ctc | ctc | tac | gac | ggc | 548 |
| His | Gly | Gly | Leu | Lys | Thr | Leu | Asp | Asp | Phe | Ala | Leu | Leu | Tyr | Asp | Gly | |
| | | | | 115 | | | | | 120 | | | | | 125 | | |
| cat | tgg | aaa | gcg | tcg | gtc | cca | gag | gga | ata | gaa | aag | ggc | atg | ctg | agc | 596 |
| His | Trp | Lys | Ala | Ser | Val | Pro | Glu | Gly | Ile | Glu | Lys | Gly | Met | Leu | Ser | |
| | | | 130 | | | | | 135 | | | | | 140 | | | |
| aac | tac | act | tcg | gac | ctg | ctc | ttt | tcc | atg | gag | cgg | ctc | tcc | aac | aac | 644 |
| Asn | Tyr | Thr | Ser | Asp | Leu | Leu | Phe | Ser | Met | Glu | Arg | Leu | Ser | Asn | Asn | |
| | | 145 | | | | | 150 | | | | | 155 | | | | |
| ccc | tac | agc | ctc | aag | cgc | ctc | cat | cca | acc | aag | gac | aag | ctg | ccg | ttc | 692 |
| Pro | Tyr | Ser | Leu | Lys | Arg | Leu | His | Pro | Thr | Lys | Asp | Lys | Leu | Pro | Phe | |
| | 160 | | | | | 165 | | | | | 170 | | | | | |
| agc | gtc | gag | gac | aag | gtg | gtc | aag | cag | ctg | acg | gcc | acg | acg | ctt | gcg | 740 |
| Ser | Val | Glu | Asp | Lys | Val | Val | Lys | Gln | Leu | Thr | Ala | Thr | Thr | Leu | Ala | |
| 175 | | | | | 180 | | | | | 185 | | | | | 190 | |
| gcg | ctc | cac | aag | gcc | ggc | cgt | ctc | ttc | ttc | gtt | gac | cac | agc | gat | cag | 788 |
| Ala | Leu | His | Lys | Ala | Gly | Arg | Leu | Phe | Phe | Val | Asp | His | Ser | Asp | Gln | |
| | | | | 195 | | | | | 200 | | | | | 205 | | |
| aag | aaa | tac | acg | ccg | cag | gca | ggt | cgg | tat | gct | gcg | gcc | tgc | cag | ggg | 836 |
| Lys | Lys | Tyr | Thr | Pro | Gln | Ala | Gly | Arg | Tyr | Ala | Ala | Ala | Cys | Gln | Gly | |
| | | | 210 | | | | | 215 | | | | | 220 | | | |
| ctt | ttc | tat | gtg | gac | gcg | cgg | tcc | aat | cag | ttc | ctg | ccg | ctg | gcc | atc | 884 |
| Leu | Phe | Tyr | Val | Asp | Ala | Arg | Ser | Asn | Gln | Phe | Leu | Pro | Leu | Ala | Ile | |
| | | 225 | | | | | 230 | | | | | 235 | | | | |
| aag | acc | aac | gtg | ggc | gca | gac | ctg | acg | tac | acg | cca | ctc | gac | gac | aag | 932 |
| Lys | Thr | Asn | Val | Gly | Ala | Asp | Leu | Thr | Tyr | Thr | Pro | Leu | Asp | Asp | Lys | |
| | 240 | | | | | 245 | | | | | 250 | | | | | |

-continued

| | |
|---|---|
| aac gac tgg ctt ctg gcc aag atc atg ttc aac aac aat gac ctg ttc<br>Asn Asp Trp Leu Leu Ala Lys Ile Met Phe Asn Asn Asn Asp Leu Phe<br>255                           260                         265                       270 | 980 |
| tac tcg cag atg tac cat gtc ctg ttc cac acg gtt cca gaa atc gtg<br>Tyr Ser Gln Met Tyr His Val Leu Phe His Thr Val Pro Glu Ile Val<br>                       275                         280                       285 | 1028 |
| cac atg gcc gcc atc cgg acg cta agc gag agc cac ccg gtg ctg gcc<br>His Met Ala Ala Ile Arg Thr Leu Ser Glu Ser His Pro Val Leu Ala<br>               290                        295                       300 | 1076 |
| gtc aat cgg atc atg tat caa gcc tat gcg atc cgg cca gtg ggc<br>Val Leu Asn Arg Ile Met Tyr Gln Ala Tyr Ala Ile Arg Pro Val Gly<br>         305                        310                       315 | 1124 |
| gaa cgc atc ctg ttc aac ccg ggc ggg ttt tgg gac cag aac ctt ggc<br>Glu Arg Ile Leu Phe Asn Pro Gly Gly Phe Trp Asp Gln Asn Leu Gly<br>320                           325                         330 | 1172 |
| ctg ccc gcc acg gcg gcc gtc gac ttt ctc agt tcc atc tac gcc cat<br>Leu Pro Ala Thr Ala Ala Val Asp Phe Leu Ser Ser Ile Tyr Ala His<br>335                           340                        345                     350 | 1220 |
| ggc gag ggc ggg ttc cgg gcc ggc tac gtg gaa aac aac ctg cgc aag<br>Gly Glu Gly Gly Phe Arg Ala Gly Tyr Val Glu Asn Asn Leu Arg Lys<br>                           355                        360                     365 | 1268 |
| cgg ggg ctg gtg ggc gac acc ttt ggc ggc ccg gcg ctc ccg cac ttc<br>Arg Gly Leu Val Gly Asp Thr Phe Gly Gly Pro Ala Leu Pro His Phe<br>          370                       375                        380 | 1316 |
| ccc ttc tac gag gac gcg cag cgc gtc ctc ggg gcg atc cgc ggc ttc<br>Pro Phe Tyr Glu Asp Ala Gln Arg Val Leu Gly Ala Ile Arg Gly Phe<br>               385                       390                       395 | 1364 |
| atg cag gcc ttt gtc gac tcg acc tac ggg ggc gac gac ggc gcg ctg<br>Met Gln Ala Phe Val Asp Ser Thr Tyr Gly Gly Asp Asp Gly Ala Leu<br>400                           405                         410 | 1412 |
| gcg cgc gac ttt gag ctg cag gac tgg gtg gcc gag gcc aac ggg ccg<br>Ala Arg Asp Phe Glu Leu Gln Asp Trp Val Ala Glu Ala Asn Gly Pro<br>415                           420                         425                     430 | 1460 |
| gcg cag gtg cgc gac ttc ccc acg gcg ccg ctg cgg cgc gag gag<br>Ala Gln Val Arg Asp Phe Pro Thr Ala Pro Leu Arg Arg Glu Glu<br>                           435                        440                     445 | 1508 |
| ctg gtg ggc atc ctg acg cac ata gcc tgg aac acg ggc ggc gcg cac<br>Leu Val Gly Ile Leu Thr His Ile Ala Trp Asn Thr Gly Gly Ala His<br>                       450                        455                     460 | 1556 |
| cac gtt cta aac cag ggg gcg ccc gtg cgc gcc tcg ggc gtg ctg ccg<br>His Val Leu Asn Gln Gly Ala Pro Val Arg Ala Ser Gly Val Leu Pro<br>               465                       470                       475 | 1604 |
| ctc cac ccg gcg gct ctt tac gcc ccc gtc ccg gcg gcc aag ggc gcc<br>Leu His Pro Ala Ala Leu Tyr Ala Pro Val Pro Ala Ala Lys Gly Ala<br>            480                        485                       490 | 1652 |
| gtc gcg tcc agc gac ggc ctg ctg gcg tgg ctg ccg gac gag gtc aaa<br>Val Ala Ser Ser Asp Gly Leu Leu Ala Trp Leu Pro Asp Glu Val Lys<br>495                           500                         505                     510 | 1700 |
| tcg gtg gag cag gtg tcg ctg ctg gcg cgc ttc aac cgc gcg cag gtt<br>Ser Val Glu Gln Val Ser Leu Leu Ala Arg Phe Asn Arg Ala Gln Val<br>                           515                        520                     525 | 1748 |
| agg gac aga aac cag acg gtg cgc aac atg ttc gcc gca ccg gag ctg<br>Arg Asp Arg Asn Gln Thr Val Arg Asn Met Phe Ala Ala Pro Glu Leu<br>                       530                        535                     540 | 1796 |
| ctg gct gga aat ggc gag gcg tac gcg gcg gcc aac gcg agg ttc gtc<br>Leu Ala Gly Asn Gly Glu Ala Tyr Ala Ala Ala Asn Ala Arg Phe Val<br>               545                       550                     555 | 1844 |
| gag gag acg ggc cgg ata agc cgc gag ata gag ggc agg ggt ttc gat<br>Glu Glu Thr Gly Arg Ile Ser Arg Glu Ile Glu Gly Arg Gly Phe Asp<br>560                           565                         570 | 1892 |

```
agc aag ggc ctg agc cag ggg atg ccc ttt atc tgg acc gcc ttg aat    1940
Ser Lys Gly Leu Ser Gln Gly Met Pro Phe Ile Trp Thr Ala Leu Asn
575             580                 585                 590 ccc gcg gtg aac ccg ttt ttc ctg agc atc tag                         1973
Pro Ala Val Asn Pro Phe Phe Leu Ser Ile
                595             600

<210> SEQ ID NO 2
<211> LENGTH: 617
<212> TYPE: PRT
<213> ORGANISM: Magnaporthe salvinii

<400> SEQUENCE: 2

Met Ar

```
Arg Ile Leu Phe Asn Pro Gly Gly Phe Trp Asp Gln Asn Leu Gly Leu
320                 325                 330                 335

Pro Ala Thr Ala Ala Val Asp Phe Leu Ser Ser Ile Tyr Ala His Gly
            340                 345                 350

Glu Gly Gly Phe Arg Ala Gly Tyr Val Glu Asn Asn Leu Arg Lys Arg
            355                 360                 365

Gly Leu Val Gly Asp Thr Phe Gly Gly Pro Ala Leu Pro His Phe Pro
        370                 375                 380

Phe Tyr Glu Asp Ala Gln Arg Val Leu Gly Ala Ile Arg Gly Phe Met
385                 390                 395

Gln Ala Phe Val Asp Ser Thr Tyr Gly Gly Asp Asp Gly Ala Leu Ala
400                 405                 410                 415

Arg Asp Phe Glu Leu Gln Asp Trp Val Ala Glu Ala Asn Gly Pro Ala
            420                 425                 430

Gln Val Arg Asp Phe Pro Thr Ala Pro Leu Arg Arg Arg Glu Glu Leu
            435                 440                 445

Val Gly Ile Leu Thr His Ile Ala Trp Asn Thr Gly Gly Ala His His
        450                 455                 460

Val Leu Asn Gln Gly Ala Pro Val Arg Ala Ser Gly Val Leu Pro Leu
465                 470                 475

His Pro Ala Ala Leu Tyr Ala Pro Val Pro Ala Ala Lys Gly Ala Val
480                 485                 490                 495

Ala Ser Ser Asp Gly Leu Leu Ala Trp Leu Pro Asp Glu Val Lys Ser
            500                 505                 510

Val Glu Gln Val Ser Leu Leu Ala Arg Phe Asn Arg Ala Gln Val Arg
            515                 520                 525

Asp Arg Asn Gln Thr Val Arg Asn Met Phe Ala Ala Pro Glu Leu Leu
        530                 535                 540

Ala Gly Asn Gly Glu Ala Tyr Ala Ala Ala Asn Ala Arg Phe Val Glu
545                 550                 555

Glu Thr Gly Arg Ile Ser Arg Glu Ile Glu Gly Arg Gly Phe Asp Ser
560                 565                 570                 575

Lys Gly Leu Ser Gln Gly Met Pro Phe Ile Trp Thr Ala Leu Asn Pro
            580                 585                 590

Ala Val Asn Pro Phe Phe Leu Ser Ile
            595                 600

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
cgcggatcca tgcgcatcgg actcttggc                                    29

<210> SEQ ID NO 4
<211> LENGTH: 31
<212> TYPE: DNA
<213> ORGANISM: Artificial Sequence
<220> FEATURE:
<223> OTHER INFORMATION: Primer

<400> SEQUENCE: 4
cccgctcgag ctagatgctc aggaaaaacg g                                 31
```

LIPOXYGENASE

CROSS-REFERENCE TO RELATED APPLICATIONS

This application is a Continuation of U.S. application Ser. No. 11/832,472 filed on Aug. 1, 2007 (now abandoned), which is a Divisional of U.S. Ser. No. 10/473,533 filed on Sep. 29, 2003 (now U.S. Pat. No. 7,264,954), which is a 35 U.S.C. 371 national application of PCT/DK02/00251 filed Apr. 18, 2002, which claims priority or the benefit under 35 U.S.C. 119 of Danish application no. PA 2001 00631 filed Apr. 20, 2001 and U.S. provisional application No. 60/286,031 filed Apr. 24, 2001, the contents of which are fully incorporated herein by reference.

FIELD OF THE INVENTION

The present invention relates to a lipoxygenase and a polynucleotide encoding it.

BACKGROUND OF THE INVENTION

Lipoxygenase (EC 1.13.11.12) is an enzyme that catalyzes the oxygenation of polyunsaturated fatty acids such as linoleic acid, linolenic acid and arachidonic acid, which contain a cis,cis-1,4-pentadiene unit and produces hydroperoxides of these fatty acids. The enzyme is widely distributed in plants and animals. A number of lipoxygenase genes have been isolated from various plant and mammalian sources.

On the other hand, only a limited number of microbial lipoxygenases are known, and no lipoxygenase gene of microbial origin has been described. Su and Oliw, J. Biological Chemistry, 273 (21), 13072-79 (1998) describe a lipoxygenase from *Gaeumannomyces graminis*.

SUMMARY OF THE INVENTION

The inventors have found a novel fungal lipoxygenase and determined its sequence, which can be used for the production of the enzyme in industrial scale. They have cloned the gene into *E. coli* and deposited the clone.

Accordingly, the invention provides a lipoxygenase which is:

a) a polypeptide encoded by a DNA sequence cloned into plasmid pUC19 present in *Escherichia coli* deposited as DSM 14139, b) a polypeptide having an amino acid sequence as the mature peptide shown in SEQ ID NO: 1, or which can be obtained therefrom by substitution, deletion, and/or insertion of one or more amino acids, c) an analogue of the polypeptide defined in (a) or (b) which:
  i) has at least 50% homology with said polypeptide,
  ii) is immunologically reactive with an antibody raised against said polypeptide in purified form,
  iii) is an allelic variant of said polypeptide, or d) a polypeptide encoded by DNA that hybridizes under low stringency conditions with a complementary strand of
  i) the DNA sequence cloned into plasmid pUC19 present in *Escherichia coli* deposited as DSM 14139 or
  ii) the DNA sequence of SEQ. ID NO: 1 encoding the mature polypeptide or a subsequence thereof having at least 100 nucleotides.

The invention also provides a polynucleotide which comprises:

a) the partial DNA sequence encoding a mature lipoxygenase cloned into a plasmid present in *Escherichia coli* DSM 14139, b) the partial DNA sequence encoding a mature lipoxygenase shown in SEQ ID NO: 1, c) an analogue of the sequence defined in a) or b) which encodes a lipoxygenase and
  i) has at least 60% homology with said DNA sequence, or
  ii) hybridizes at high stringency with a complementary strand of said DNA sequence or a subsequence thereof having at least 100 nucleotides,
  iii) is an allelic variant thereof, or d) a complementary strand of a), b) or c).

Other aspects of the invention provide a nucleic acid construct and a recombinant expression vector comprising the polynucleotide, a recombinant host cell comprising the construct or the vector, and a method of producing a lipoxygenase by cultivating the cell. Further, the invention provides a method of screening a eukaryotic library to obtain a lipoxygenase and an oligonucleotides probe useful for screening. Finally, the invention provides use of the lipoxygenase in baking and in a detergent.

DETAILED DESCRIPTION OF THE INVENTION

Genomic DNA Source

A lipoxygenase gene of the invention may be derived from a filamentous fungus, e.g. an Ascomycota, particularly Magnaporthaceae, such as a strain of *Magnaporthe*, particularly *Magnaporthe salvinii* Cattaneo (*Mycologia* 64 (1), 110 (1972)). The species is also known under the synonyms *Curvularia sigmoides, Helminthosporium sigmoideum, Leptosphaeria salvinii, Nakataea sigmoidea, Sclerotium oryae* and *Vakrabeeja sigmoidea*. An example is the strain *M. salvinii* IFO 6642.

Alternatively, the gene may be isolated from *Pyricularia*, e.g. *P. oryzae* or *P. grisea*, e.g. *P. oryzae* IFO 30517. The IFO strains are available on commercial terms from Institute for Fermentation, Osaka (IFO), 17-85, Juso-honmachi 2-chome, Yodogawa-ku, Osaka 532-8686, Japan.

The lipoxygenase gene may be isolated from these organisms using probes designed on the basis of the DNA sequences in this specification.

A strain of *Escherichia coli* containing a lipoxygenase gene from *M. salvinii* IFO 6642 was deposited by the inventors under the terms of the Budapest Treaty with the DSMZ—Deutsche Sammmlung von Microorganismen und Zellkulturen GmbH, Mascheroder Weg 1b, D-38124 Braunschweig DE, Germany. The deposit date was 28 Feb. 2001, and the accession number was DSM 14139.

Production of Lipoxygenase by Cultivation of Transformant

The lipoxygenase of the invention may be produced by transforming a suitable host cell with a DNA sequence encoding the lipoxygenase, cultivating the transformed organism under conditions permitting the production of the enzyme, and recovering the enzyme from the culture.

The host organism may be a eukaryotic cell, in particular a fungal cell, such as a yeast cell or a filamentous fungal cell, e.g. a strain of *Aspergillus, Fusarium, Trichoderma* or *Saccharomyces*, particularly *A. niger, A. oryzae, F. graminearum, F. sambucinum, F. cerealis* or *S. cerevisiae*. The production of the lipoxygenase in such host organisms may be done by the general methods described in EP 236,023 (Novo Nordisk), WO 96/00787 (Novo Nordisk) or EP 244,234 (Alko).

Properties of LOX

The lipoxygenase of the invention is able to oxidize a wide range of substrates containing a cis-cis-pentadienyl moiety.

Thus, it acts on polyunsaturated fatty acids such as linoleic acid (18 carbon atoms, 2 double bonds), linolenic acid (18:3), arachidonic acid (20:4), eicosapentaenoic acid (EPA, 20:5) and docosahexaenoic acid (DHA, 22:6). It also acts on substrates other than fatty acids, such as methyl linoleate and probably also triglycerides. The enzyme has a very low Michaelis constant ($K_M$) for linoleic acid and a high specificity ($V_{max}/K_M$) towards this substrate.

The lipoxygenase from *M. salvinii* is a 9-lipoxygenase, i.e. it oxidizes the double bond between carbon atoms 9 and 10 in linoleic acid and linolenic acid.

The lipoxygenase from *M. salvinii* has optimum activity around pH 7, and it is highly active over a broad pH range 3-12, having more than 50% of optimum activity in the range pH 6-11. It is stable after overnight incubation at pH 5-11.

The native lipoxygenase from *M. salvinii* has optimum activity at 50-60° C. It is quite active at 40-60° C., and the activity begins to decline at 70° C. The lipoxygenase is stable after 30 minutes incubation at pH 7 at temperatures up to 50° C.

The reaction rate for recombinant lipoxygenase (expressed in *A. oryzae*) increases nearly ten times at the optimal temperature for catalysis compared to the rate obtained at room temperature. The maximum reaction rate is obtained at 67.5° C. A steep decrease in rate constant is seen above the temperature optimum. It is believed that glycosylation renders the recombinant enzyme more stable towards heat than the wild-type enzyme.

The recombinant lipoxygenase is quite stable at temperatures up to 50° C. for at least one hour. The activity drops in a linear fashion at higher temperatures between 50-60° C., and no activity is detected after incubations above 60° C. for one hour. No activity loss is detected during incubation at temperatures below 45° C.

Frozen solutions of the lipoxygenase lose some activity during storage. With addition of 10% glycerol there is no discernible activity loss after two weeks storage at −20° C., and the enzyme survived repeated cycles of thaw-freeze without loss of activity.

The lipoxygenase of the invention has good stability in the presence of anionic surfactants. Thus, the lipoxygenase from *M. salvinii* is stable in the presence of 400 ppm of LAS (linear alkyl-benzene sulfonate).

Use of Lipoxygenase

The lipoxygenase can be used for green flavor synthesis, e.g. nonenal from 9-hydroperoxide of linolenic acid. The synthesis may be done in analogy with Whitehead et al. 1995, Cereal foods world 40(4), 193-197 and U.S. Pat. No. 4,768,243.

The lipoxygenase can also be used for plant hormone synthesis as described in JP H11-29410.

Also the lipoxygenase is a good oxidant of carotenoids, so it can be used for bleaching of foodstuffs such as flour, oil or marine food including carotenoids or carotenoid-like pigments.

The oxidation activity can be utilized for cross-linking of protein, oil, starch, fiber and mixture of these. Cross-linking of chemical compounds can be utilized for synthesis of polymer to give plastic fiber or plastic resin. It can be used for bleaching as a detergent for phenolic, carotenoid or fatty stains or dinginess. Or it can be used for bleaching of waste water or textile dye.

Lipoxygenase can be used for bleaching of plant or marine food materials containing of carotenoids. Thus it could be used for bleaching of flour for bread, noodle or pasta, or bleaching of fish meat or fish oil containing astaxanthin.

It also can be used for cross-linking of protein, oil, starch, plant-fiber or mixture of these in presence of fatty acid, oil or fats. It is useful to change the texture or physical properties of foodstuff or to control of flavor for fat and oil, or to produce polymers made of natural staff beside food use. Cross-linked compounds can be chemical compounds, e.g. phenolic, carbonyl, carboxyl or amide compounds or mixture of these. It could be used for synthesis of plastic fiber or resin.

Other usages of lipoxygenase can be the synthesis of flavor compound such as hexanal or hexenal together as synergy effect of hydroperoxide lyase. Or in case plant material is used as the source of above two enzymes, lipoxygenase can be added to it to improve the yield of flavor compound. The similar can be done for synthesis of plant or animal hormones.

Finally it can be used as bleaching agent. It can be used in detergents for bleaching of phenolic, carotenoid, fatty stains or dinginess of clothes. Or it can be used for bleaching of textile dye or dye for pulp industry in waste water or changing of dye texture.

Recombinant Expression Vector

The expression vector of the invention typically includes control sequences encoding a promoter, operator, ribosome binding site, translation initiation signal, and, optionally, a selectable marker, a transcription terminator, a repressor gene or various activator genes. The vector may be an autonomously replicating vector, or it may be integrated into the host cell genome.

Production by Cultivation of Transformant

The lipoxygenase of the invention may be produced by transforming a suitable host cell with a DNA sequence encoding the lipoxygenase, cultivating the transformed organism under conditions permitting the production of the enzyme, and recovering the enzyme from the culture.

The host organism may be a eukaryotic cell, in particular a fungal cell, such as a yeast cell or a filamentous fungal cell, e.g. a strain of *Aspergillus, Fusarium, Trichoderma* or *Saccharomyces*, particularly *A. niger, A. oryzae, F. graminearum, F. sambucinum, F. cerealis* or *S. cerevisiae*. The production of the lipoxygenase in such host organisms may be done by the general methods described in EP 238,023 (Novo Nordisk), WO 96/00787 (Novo Nordisk) or EP 244,234 (Alko).

The enzyme can be purified in one step by cation-exchange chromatography to homogeneity.

Nucleotide Probe

A nucleotide probe may be designed on the basis of the DNA sequence of SEQ ID NO: 1 or the polypeptide sequence of SEQ ID NO: 2, particularly the mature peptide part. The probe may be used in screening for LOX-encoding DNA as described below.

A synthetic oligonucleotide primer may be prepared by standard techniques (e.g. as described in Sambrook J, Fritsch E F, Maniatis T (1989) Molecular cloning: a laboratory manual ($2^{nd}$ edn.) Cold Spring Harbor Laboratory, Cold Spring Harbor, N.Y.) on the basis of the mature part of the amino acid sequence in SEQ ID NO: 2 or the corresponding part of the DNA sequence. It may be a degenerate probe and will typically contain at least 20 nucleotides.

Screening of Eukaryotic DNA Library

A polypeptide with lipoxygenase activity may be obtained by a method comprising:

a) preparing a eukaryotic DNA library, b) screening the library to select DNA molecules which hybridize to the probe described above, c) transforming host cells with the selected DNA molecules, d) cultivating the transformed host cells to express polypeptides encoded by the DNA molecules, and e) assaying the expressed polypeptides to select polypeptides having lipoxygenase activity.

The eukaryotic DNA library may be prepared by conventional methods. It may include genomic DNA or double-stranded cDNA derived from suitable sources such as those described above.

Molecular screening for DNA sequences may be carried out by polymerase chain reaction (PCR) followed by hybridization.

In accordance with well-known procedures, the PCR fragment generated in the molecular screening may be isolated and subcloned into a suitable vector. The PCR fragment may be used for screening DNA libraries by e.g. colony or plaque hybridization.

Hybridization

The hybridization is used to indicate that a given DNA sequence is analogous to a nucleotide probe corresponding to a DNA sequence of the invention. The hybridization may be done at low, medium or high stringency. One example of hybridization conditions is described in detail below.

Suitable conditions for determining hybridization between a nucleotide probe and a homologous DNA or RNA sequence involves presoaking of the filter containing the DNA fragments or RNA in 5×SSC (standard saline citrate) for 10 min, and prehybridization of the filter in a solution of 5×SSC (Sambrook et al. 1989), 5×Denhardt's solution (Sambrook et al. 1989), 0.5% SDS and 100 µg/ml of denatured sonicated salmon sperm DNA (Sambrook at al. 1989), followed by hybridization in the same solution containing a random-primed (Feinberg, A. P. and Vogelstein, B. (1983) *Anal. Biochem.* 132:6-13), $^{32}$P-dCTP-labeled (specific activity >1×10$^9$ cpm/µg) probe for 12 hours at approx. 45° C. The filter is then washed two times for 30 minutes in 2×SSC, 0.5% SDS at a temperature of at least 55° C., particularly at least 60° C., more particularly at least 65° C., e.g. at least 70° C., or at least 75° C.

Molecules to which the oligonucleotide probe hybridizes under these conditions are detected using an x-ray film.

Alignment and Homology

The lipoxygenase and the nucleotide sequence of the invention may have homologies to the disclosed sequences of at least 75% or at least 85%, particularly at least 90% or at least 95%, e.g. at least 98%.

For purposes of the present invention, alignments of sequences and calculation of homology scores were done using a Needleman-Wunsch alignment (i.e. global alignment), useful for both protein and DNA alignments. The default scoring matrices BLOSUM50 and the identity matrix are used for protein and DNA alignments respectively. The penalty for the first residue in a gap is –12 for proteins and –16 for DNA, white the penalty for additional residues in a gap is –2 for proteins and –4 for DNA. Alignment is from the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 183:63-98).

EXAMPLES

Materials and Methods

Molecular cloning techniques are described in Sambrook at al. (1989).

The following commercial plasmids and *E. coli* strains were used for sub-cloning and DNA library construction:
pT7Blue (Novagen)
pUC19 (TOYOBO, Japan)
*E. coli* JM109 (TOYOBO, Japan)
*E. coli* DH12S (GIBCO BRL, Life Technologies, USA)

Labeling and detection of hybridization probe was done using DIG-labeling and detection Kit (Boehringer Mannheim). Nylon membrane Hybond-N+ (Amersham, England) was used for DNA transfer for colony hybridization.

Soybean lipoxygenase (type I-B) (cat. # L7315) and astaxanthin (cat. # A-9335) was supplied by Sigma. b-carotene (cat. # 031-05533) were supplied by Wako.

Media and Buffer Solution

COVE-ar: per liter 342.3 g sucrose, 20 ml COVE salt solution, 10 mM acryl amide, 15 mM CsCl$_2$, 30 g Agar noble (Difco)

COVE2-ar: per liter 30 g sucrose, 20 ml COVE salt solution, 10 mM acrylamide, 30 g Agar noble (Difco)

COVE salt solution: per liter 26 g KCl, 26 g MgSO$_4$-7H$_2$O, 76 g KH$_2$PO$_4$, 50 ml Cove trace metals.

Cove trace metals: per liter 0.04 g NaB$_4$O$_7$-10H$_2$O, 0.4 g CuSO$_4$-5H$_2$O, 1.2 g FeSO$_4$-7H$_2$O, 0.7 g MnSO$_4$—H$_2$O, 0.7 g Na$_2$MoO$_2$-2H$_2$O, 0.7 g ZnSO$_4$-7H$_2$O.

AMG trace metals: per liter 14.3 g ZnSO$_4$-7H$_2$O, 2.5 g CuSO$_4$-5H$_2$O, 0.5 g NiCl$_2$, 13.8 g FeSO$_4$, 8.5 g MnSO$_4$, 3.0 g citric acid.

YPG: per liter 4 g yeast extract, 1 g KH$_2$PO$_4$, 0.5 g MgSO$_4$7H$_2$O, 15 g glucose, pH 6.0.

STC: 0.8 M Sorbitol, 25 mM Tris pH 8, 25 mM CaCl$_2$.

STPC: 40% PEG4000 in STC buffer.

Cove top agarose: per liter 342.3 g sucrose, 20 ml COVE salt solution, 10 mM Acetamide, 10 g low melt agarose.

MS-9: per liter 30 g soybean powder, 20 g glycerol, pH 6.0.

MDU-2 Bp: per liter 45 g maltose-1H$_2$O, 7 g yeast extract, 12 g KH$_2$PO$_4$, 1 g MgSO$_4$-7H$_2$O, 2 g K$_2$SO$_4$, 5 g Urea, 1 g NaCl, 0.5 ml AMG trace metal solution pH 5.0.

Host Organism

*Aspergillus oryzae* BECh2 is described in WO 00/39322. It is a mutant of JaL228 (described in WO98/123000), which is a mutant of IFO4177.

Transformation of *A. oryzae*

*Aspergillus oryzae* strain BECh2 was inoculated in 100 ml of YPG medium and incubated at 32° C. for 16 hours with stirring at 80 rpm. Grown mycelia was collected by filtration followed by washing with 0.6 M KCl and re-suspended in 30 ml of 0.6 M KCl containing Glucanex® (Novozymes) at the concentration of 30 µl/ml. The mixture was incubated at 32° C. with the agitation at 60 rpm until protoplasts were formed. After filtration to remove the remained mycelia, protoplasts were collected by centrifugation and washed with STC buffer twice. The protoplasts were counted with a hematitometer and re-suspended in a solution of STC:STPC:DMSO (8:2:0.1) to a final concentration of 1.2×10$^7$ protoplasts/ml. About 4 µg of DNA was added to 100 µl of protoplast solution, mixed gently and incubated on ice for 30 minutes. 1 µl STPC buffer was added to the mixture and incubated at 37° C. for another 30 minutes. After the addition of 10 ml of Cove top agarose pre-warmed at 50° C., the reaction mixture was poured onto COVE-ar agar plates. The plates were incubated at 32° C. for 5 days.

SDS-PAGE

SDS polyacrylamide electrophoresis was carried out using the commercialized gel PAGEL AE6000 NPU-7.5L (7.5T %) with the apparatus AE-6400 (Atto, Japan) following the provided protocol. 15 µl of sample was suspended in 15 µl of 2× conc. of sample loading buffer (100 mM Tris-HCl (pH 6.8), 200 mM Dithiothreitol, 4% SDS, 0.2% Bromophenol blue and 20% glycerol) and boiled for 5 minutes. 20 µl of sample solution was applied to a polyacrylamide gel, and subjected for electrophoresis in the running buffer (25 mM Tris, 0.1%

SOS, 192 mM Glycine) at 20 mA per gel. Resulting gel was stained with SYPRO Orange and detected by molecular Imager FX (BIO-RAD).

Assays for Lipoxygenase Activity

Spectrophotometric Assay

Lipoxygenase activity was determined spectrophotometrically at 25° C. by following the formation of hydroperoxides with the absorbance at 234 nm. To 0.98 ml of the buffer (50 mM $KH_2PO_4/NaHPO_4$, pH 7.0), 10 µl of substrate solution (10 mM linolenic acid dispersed with 0.2% Tween20) was added and the reaction was started by the addition of 10 µl of enzyme solution. One unit causes an increase in absorbance at 234 nm of 0.001/min.

FOX Assay

The assay was initiated by the addition of 20 µl enzyme solution to 80 µl of 50 mM each buffer containing 0.7 mM linolenic acid dispersed with 0.02% of Tween 20 using Hiscotron, and incubated for 10 min. The assay was terminated by the addition of 900 µl of FOX reagent: sulfuric acid (25 mM), xylenol orange (100 µM), iron(II) sulfate (100 µM), butylated hydroxytoluen (4 mM) in methanol:water (9:1). Blanks contained only substrate solution during the incubation, but enzyme solution was added after the addition of FOX reagent. The yellow color of acidified xylenol, orange was converted to a blue color by the lipid hydroperoxide-mediated oxidation of $Fe^{2+}$ ions with the dye. Absorbance of the $Fe^{3+}$ complex at 620 nm was measured 1 hour after the addition of FOX reagent.

Bleaching Assay

Bleaching effect by lipoxygenase was examined spectrophotometrically at 25° C. by following the absorbance at 470 nm. The pigment solution was prepared as follows. 150 ul of stock pigment solution (1 mg each pigment in 1 ml chloroform) was evaporated to be dry. Then 30 ml of the buffer (50 mM $KH_2PO_4/NaHPO_4$, pH 7.0) with 0.3% of Tween 20 was added slowly and the pigment was dissolved. To 0.98 ml of the pigment solution, 10 µl of substrate solution (10 mM linolenic acid dispersed with 0.2% of Tween20) was added and the reaction was started by the addition of 10 µl of enzyme solution.

Example 1

Cloning of Genomic LOX Gene from *M. salvinii*

Genomic DNA from *Magnaporthe salvinii* was digested with Sac I and separated on 1.0% agarose gel. Around 2.5 kbp of DNA digestion was recovered from the gel and ligated with BAP treated pUC19 linearized by Sac I. Ligation mixture was transformed into *E. coli* DH12S to construct a partial genomic library. It was screened, and a lipoxygenase-positive *E. coli* colony was isolated and the plasmid, termed pSG28, was recovered. The plasmid pSG28 contained a 2.5 kbp SacI genomic fragment that contained the presumed LOX homologue sequence. The sequence of 1973 bp out of 2.5 kbp is shown as SEQ. ID 1.

Introns were identified and are indicated in SEQ ID NO: 1. The splice sites were predicted as described in S. M. Hebsgaard et al., Nucleic Acids Research, 1996, Vol. 24, No. 17, 3439-3452.

The presumed open reading frame consisted of 1851 bp, and the deduced amino acid sequence corresponded to 617 amino acids, shown as SEQ ID NO: 2. The molecular mass was estimated as 67500 Da.

The *E. coli* DH12S harboring plasmid pSG28 was deposited at DSMZ as DSM 14139 with the accession date 2001 Feb. 28.

Example 2

Expression of *M. salvinii* LOX in *A. oryzae*

Construction of Expression Plasmid

The partial genomic sequence of *M. salvinii* genomic gene was amplified by PCR using pSG28 as a template. Primer 3 and 4 (SEQ ID NO: 3 and 4) were designed to make BamH I and Xho I sites at both ends of the PCR product (nucleotides 4-9 of primer 3 and 5-10 of primer 4, respectively). PCR reaction mixture comprised of 2.5 mM dNTP, 30 pmol each of primer 3 and 4, 5 units of LA taq polymerase (Takara) and supplied GC buffer I. Reaction condition was shown below. LA taq polymerase was added to the reaction mixture after step 1.

| Step | Temperature | Time |
| --- | --- | --- |
| 1 | 98° C. | 10 mins |
| 2 | 96° C. | 20 sec |
| 3 | 55° C. | 45 sec |
| 4 | 72° C. | 30 sec |
| 5 | 72° C. | 10 mins |

* Step 2 to Step 4 were repeated 30 times.

PCR amplified 1.9 kb fragment was isolated and cloned into pT7Blue resulting in pSG29.

The plasmid pSG29 was digested by BamHII and XhoI and 1.9 kb of fragment which contained the LOX gene was ligated with pMT2188 digested with BamHI and XhoI. The plasmid pMT2188 has a modified *Aspergillus niger* neutral amylase promoter, *Aspergillus nidulans* TPI leader sequence, *Aspergillus niger* glucoamylase terminator, *Aspergillus nidulans* amdS gene as a marker for fungal transformation and *S. cerevisiae* ura3 as the marker for *E. coli* transformation. Transformation was done with *E. coli* DB6507 in which pyrF gene is deficient and can be complemented with *S. cerevisiae* Ura3. Resulting plasmid was termed pSG30.

Expression of *M. salvinii* LOX in *A. oryzae*

*A. oryzae* BECh2 was transformed with the plasmid pSG30 and selection positive transformants were isolated. Transformants were grown on COVE 2-ar at 32° C. for 5 days and inoculated to 100 ml of MS-9 shaking flask. After the cultivation with vigorous agitation at 32° C. for 1 day, 3 ml of each culture was transferred to 100 ml of MDU-2Bp in shaking flask to cultivate at 32° C. for 3 days. Culture broth was centrifuged at 3500 rpm for 10 minutes and supernatant was collected.

Lipoxygenase activities of the supernatant were determined spectrophotometrically as described before. Positive transformants showed about 100,000 U/ml culture broth while untransformed *A. oryzae* BECh2 showed no activity. Culture supernatant was also subjected to SDS-PAGE analysis. Positive transformants showed 80-100 kDa smear band which indicated the protein was heavily glycosylated. Untransformed *A. oryzae* BECh2 did not show any significant bands.

Example 3

Substrate Specificity of Lipoxygenase

Kinetic parameters for a number of substrates were determined by standard methods for the *M. salvinii* lipoxygenase.

| Substrate | $V_{max}$ (μmol/min/mg) | $K_M$ (μM) | $V_{max}/K_M$ (μmol/min/mg/μM) |
|---|---|---|---|
| Linoleic acid | 2.63 | 1 | 2.557 |
| Na linoleate | 2.07 | 0.41 | 5.061 |
| Linoelaidic acid | No activity | No activity | No activity |
| Linolenic acid | 1.9 | 0.4 | 4.488 |
| Eicosadienoic acid | 2.02 | 11 | 0.177 |
| Arachidonic acid | 2.44 | 5.5 | 0.446 |
| Linoleoyl chloride | 0.97 | 12 | 0.080 |
| Methyl linoleate | 0.82 | 30 | 0.026 |
| Linoleoyl acetate | 0.77 | 9 | 0.085 |
| Linoleoyl alcohol | 1.4 | 8 | 0.175 |

For comparison, one substrate was also tested with soybean lipoxygenase.

| Substrate | $V_{max}$ (μmol/min/mg) | $K_M$ (μM) | $V_{max}/K_M$ (μmol/min/mg/μM) |
|---|---|---|---|
| Linoleic acid | 12.3 | 230 | 0.054 |

Example 3 pH Dependence of Lipoxygenase Activity

The relative activity of the *M. salvinii* lipoxygenase at various pH values was determined by the FOX assay described above, using the following buffers: 50 mM citric acid/sodium citrate (pH 2.21-3.73), $KH_2PO_4/Na_2HPO_4$ (pH 5.30, 6.17), Tris/HCl (pH 7.01, 8.02), glycylglycine NaCl/NaOH (pH 9.33-11.0).

| pH | Relative Activity (%) |
|---|---|
| 2.21 | 7.11 |
| 2.90 | 20.6 |
| 3.73 | 27.7 |
| 5.30 | 60.0 |
| 6.17 | 83.7 |
| 7.01 | 100 |
| 8.02 | 92.9 |
| 9.33 | 82.6 |
| 11.0 | 77.7 |

Example 4

Temperature Dependence of Lipoxygenase Activity

The effect of temperature on the *M. salvinii* lipoxygenase was studied by 10 min incubation at pH 7.0.

| Temperature | Relative Activity (%) |
|---|---|
| 25 | 50.1 |
| 40 | 90.0 |
| 50 | 100 |
| 60 | 99.6 |
| 70 | 60.4 |

Example 5

Bleaching Effect of Lipoxygenases

The bleaching effect of *M. salvinii* LOX was examined. Soybean L1 was included for comparison. β-carotene and astaxanthin were used as pigments.

| β-carotene | Time (min) | *M. salvinii* | Soybean L1 |
|---|---|---|---|
| | 0 | 0.3783 | 0.3575 |
| | 0.4 | 0.3791 | 0.3616 |
| | 0.8 | 0.3729 | 0.3601 |
| | 1.2 | 0.3702 | 0.362 |
| | 1.4 | 0.3685 | 0.3602 |
| | 1.8 | 0.3651 | 0.3602 |
| | 2.2 | 0.3633 | 0.3595 |
| | 2.6 | 0.3486 | 0.3595 |
| | 3 | 0.341 | 0.3594 |
| ΔA470/min | | 0.0121 | 0.00005 |
| LOX activity | | 2.652 | 1.962 |

| Astaxanthin | Time (min.) | *M. salvinii* | Soybean L1 |
|---|---|---|---|
| | 0 | 0.5292 | 0.5026 |
| | 0.4 | 0.5244 | 0.5029 |
| | 0.8 | 0.5177 | 0.505 |
| | 1 | 0.5166 | 0.5025 |
| | 1.4 | 0.512 | 0.5013 |
| | 1.8 | 0.5004 | 0.4993 |
| | 2.2 | 0.4876 | 0.4985 |
| | 2.6 | 0.4714 | 0.4986 |
| | 3 | 0.4566 | 0.498 |
| ΔA470/min | | 0.0239 | 0.0021 |
| LOX activity | | 2.4952 | 2.018 |

The results show that *M. salvinii* LOX bleaches the pigment solutions. Soybean LOX showed little effect on bleaching.

The invention claimed is:

1. An isolated lipoxygenase having an amino acid sequence which has at least 90% homology with a polypeptide having an amino acid sequence of the polypeptide of amino acids 1-600 of SEQ ID NO: 2.

2. The lipoxygenase of claim 1 which is obtained from a filamentous fungus.

3. The lipoxygenase of claim 1 which is obtained from an Ascomycota.

4. The lipoxygenase of claim 1 which is obtained from *Magnaporthe*.

5. The lipoxygenase of claim 1 which is obtained from *M. salvinii*.

6. The lipoxygenase of claim 1 which is obtained from *M. salvinii* strain IFO 6642.

7. The lipoxygenase of claim 1 which is encoded by a DNA sequence cloned into plasmid pUC19 present in *Escherichia coli* deposited as DSM 14139.

8. The lipoxygenase of claim 1 which has at least 95% homology with a polypeptide having an amino acid sequence of the polypeptide of amino acids 1-600 of SEQ ID NO: 2.

9. A method for preparing a dough or a baked product made from dough, comprising adding the lipoxygenase of claim 1 to the dough.

10. A dough composition comprising the lipoxygenase of claim 1.

11. A detergent composition comprising a surfactant and the lipoxygenase of claim 1.

12. The detergent composition of claim 11 wherein the surfactant is anionic.

13. A process for oxidizing a polyunsaturated fatty acid comprising contacting the acid with the lipoxygenase of claim 1 in the presence of air.

* * * * *